United States Patent [19]
Bright et al.

[11] Patent Number: 5,807,107
[45] Date of Patent: Sep. 15, 1998

[54] DENTAL INFECTION CONTROL SYSTEM

[75] Inventors: Billy J. Bright; Steven L. Dacus, both of Casper, Wyo.

[73] Assignee: Barrier Supply, Casper, Wyo.

[21] Appl. No.: 731,875

[22] Filed: Oct. 18, 1996

Related U.S. Application Data

[60] Provisional application No. 60/005,777, Oct. 20, 1995.
[51] Int. Cl.$^6$ ........................................................ A61C 1/16
[52] U.S. Cl. ............................................... 433/116; 433/29
[58] Field of Search .............................. 433/29, 116, 229; 600/119, 121, 122, 124

[56] References Cited

U.S. PATENT DOCUMENTS

| | | | |
|---|---|---|---|
| 1,742,061 | 12/1929 | Curry | 433/116 |
| 4,266,935 | 5/1981 | Hoppe | 433/116 |
| 4,385,344 | 5/1983 | Gonser | 433/29 |
| 4,723,912 | 2/1988 | Nieusma | 433/116 |
| 4,757,381 | 7/1988 | Cooper et al. | 358/98 |
| 4,795,343 | 1/1989 | Choisser | 433/116 |
| 4,810,194 | 3/1989 | Snedden | 433/91 |
| 4,975,826 | 12/1990 | Bell | 362/376 |
| 4,998,880 | 3/1991 | Nerli | 433/80 |
| 5,142,736 | 9/1992 | Kuehn et al. | 16/111 R |
| 5,217,370 | 6/1993 | Craig et al. | 433/116 |
| 5,302,124 | 4/1994 | Lansing et al. | 433/116 |
| 5,328,368 | 7/1994 | Lansing et al. | 433/116 |
| 5,337,734 | 8/1994 | Saab | 600/121 |
| 5,359,991 | 11/1994 | Takahashi et al. | 600/122 |
| 5,487,661 | 1/1996 | Peithman | 433/116 |

FOREIGN PATENT DOCUMENTS

| | | | |
|---|---|---|---|
| 539315 | 4/1993 | European Pat. Off. | 433/29 |
| 2218636 | 11/1989 | United Kingdom | 433/116 |

OTHER PUBLICATIONS

Cover page of U.S. Patent 4,266,935.
Cover page of U.S. Patent 4,615,679.
Cover page of U.S. Patent 4,693,871.
Cover page of U.S. Patent 4,723,912.
Cover page of U.S. Patent 4,728,290.
Cover page of U.S. Patent 4,777,574.
Cover page of U.S. Patent 4,859,182.
Cover page of U.S. Patent 4,880,381.
Cover page of U.S. Patent 4,907,968.
Cover page of U.S. Patent 4,998,880.
Cover page of U.S. Patent 5,607,899.
Cover page of U.S. Patent 5,139,422.
Cover page of U.S. Patent 5,197,875.
Cover page of U.S. Patent 5,222,600.
Cover page of U.S. Patent 5,228,851.
Cover page of U.S. Patent 5,267,860.
Cover page of U.S. Patent 5,288,231.

*Primary Examiner*—Cary E. O'Connor
*Attorney, Agent, or Firm*—Santangelo Law Offices, P.C.; William F. Vobach

[57] ABSTRACT

A dental infection control system utilizing barrier protection to prevent cross-contamination between patients is disclosed. A unitary cover is provided for covering a piece of dental equipment to provide not only barrier protection but also ventilation openings for the device being protected. The unitary cover can be configured to position ventilation openings in the cover in proximity to any ventilation openings on the equipment being protected. A cover can be used to establish and maintain a multipieced instrument in compression and facilitate the operation of the instrument. A cover allows a transparent material to be placed in tension over a fiber optic portion of an instrument and reduce corruption of the light emitted from the instrument. In addition, provision is made to reverse the cover to reduce the possibility of contaminating the instrument when the cover is removed.

56 Claims, 13 Drawing Sheets

5,807,107

DENTAL INFECTION CONTROL SYSTEM

This application claims the benefit of application 60/005,777, filed on Oct. 20, 1995. The contents of that application are hereby incorporated by reference.

BACKGROUND OF THE INVENTION

This invention relates to the field of dental infection or, cross-contamination control systems. Specifically, it relates to the area of preventing the spread of germs, disease, or infection through the use of dental equipment, such as a dental curing light.

Infection control and cross-contamination prevention in dental offices is a significant issue that must be addressed by professionals working in such areas on a daily basis. Infection or disease can be easily spread through dental instruments which are utilized over and over again on different patients. When diseases are spread in this manner, it is referred to as cross-contamination. It is essential that instruments be protected and cleaned so that germs or disease are not spread from one patient to another. Furthermore, various federal, state, and local regulations, including OSHA guidelines, have been passed in regard to cross-contamination requiring dental personnel to take steps that will reduce this danger.

Various methods have been used in the past in an attempt to prevent cross-contamination. One such method involves the use of chemical disinfectants, usually in spray form. In such a method, a disinfectant can be applied to a piece of equipment and allowed to sit for a period of time. The disinfectant can then be removed by being cleaned or wiped off. This regimen is followed after each procedure, before the next patient is seen. A second method utilizes a disposable protective barrier over an item that is to be protected or over a specific area of such an item that is subject to contamination. After an instrument covered by such a barrier is used on a patient, the barrier can be removed and a new barrier can be applied to the instrument for use in the next procedure. Most dental offices use one of these two methods (chemical disinfectants or disposable protective barriers) to provide infection control and to prevent cross-contamination.

Many dental offices have found that the chemical disinfection method has several disadvantages. Among these potential drawbacks is the amount of time it takes to disinfect the equipment with the chemical disinfectant, which results in a longer turn around time between patients because of the waiting period. Furthermore, it has been found that repeated, prolonged use of disinfectant sprays can cause a buildup of residue on the equipment. In addition, the sprays can also cause problems in the electrical circuitry of the devices themselves. For example, problems can be caused in the switches and delicate electrical components of the dental equipment. Therefore, barrier protection is often preferred. However, in regard to some pieces of equipment barrier protection has been difficult to implement.

One instrument commonly found in dental offices is a device known as a dental curing light. Dental curing lights are used to cure cements or other light sensitive materials that are often used in dental procedures such as when applying braces on children's teeth. The characteristics of the light emitted from a dental curing light, when the light is directed at the cement, cause the cement to harden or cure. Use of a dental curing light requires that the dental curing light be inserted into a patient's mouth. Therefore, it is a likely candidate for spreading germs and disease from one patient to another. Dental curing lights are available in several different brands, models, styles, sizes, etc. However, they have certain fundamental features in common. These features include a body (i.e., housing or handling unit) portion, a fiber optic light probe portion, and a tip portion at the end of the fiber optic light probe portion (from which light is emitted). The dental curing light light probe portion is attached to the dental curing light body portion when used on a patient. Within the housing unit are typically a light source (which also acts as a heat producing element), a switching mechanism, and a ventilation or cooling system. The ventilation system consists of various elements including air intake vent openings or ducts, a cooling fan and motor, and exhaust vent openings or ducts (which also serve as heat producing elements). It is often necessary to allow air to circulate through this ventilation system to provide proper cooling of the dental light curing instrument.

Because intake openings and exhaust openings are often located on the body of an instrument, like a dental curing light, it has been difficult to provide both adequate shielding of the instrument and sufficient ventilation of the instrument through the use of plastic barriers. Attempts to use barriers on dental curing lights in the past have either erred on the side of not providing sufficient barrier protection of the dental curing light due to not covering enough surface area of the dental curing light (in an attempt to provide sufficient ventilation) or have erred in not providing adequate ventilation of the dental curing light due to covering too much of the dental curing light's ventilation openings (in an attempt to provide sufficient barrier protection).

Perhaps the most significant drawback encountered in previous designs for dental curing light barriers is the fact that two separate covers were used—a first cover to shield the dental curing light fiber optic probe and a second cover to shield the dental curing light body (i.e., housing or handle unit). This may have been done so that the ventilation openings on the dental curing light remained exposed to the environment. This method is undesirable for a number of reasons. First, the cover for the dental curing light probe is a relatively loose fitting sheath that has a tendency to move or bunch up. This is unsatisfactory because it fails to shield or cover the dental curing light probe sufficiently and as a result allows germs to contact the probe. Furthermore, as this sheath moves, it is moved away from the light probe tip. By moving away from the light probe tip, the sheath no longer presents as transparent a surface, in comparison to its preferred position, and thus causes degradation of the light emission from the light probe. To combat this movement, an attachment is usually needed to attempt to secure the cover for the dental curing light probe to the probe. This adds yet another time consuming step to the process of shielding a dental curing light. It also highlights another problem encountered in this process, i.e., the amount of time and effort required to install and then remove the first cover, the second cover and any attachment for the first cover. Another drawback is the expense in providing two covers rather than one. Furthermore, installation of more than one barrier provides ample opportunity for error which results in a greater opportunity for cross-contamination to occur. As a result, there is a need for an effective barrier control system that permits ventilation of equipment such as light curing equipment but does not involve the use of multiple plastic barriers. Furthermore, these drawbacks highlight the fact that there has been a longfelt need for a solution to these problems that those of ordinary skill in the art appear to have been unable to satisfy. In fact, previous attempts to shield some devices have actually gone in different directions from the present invention, thus highlighting the novelty of the present invention.

As noted above, a significant problem with existing methods of barrier protection on fiber optic instruments is the fact that when the barrier is not held smooth against the surface of the optical instrument, the light emitted from the instrument can be degraded. Therefore, it is necessary to establish and maintain the barrier in tension across the fiber optic instrument in order to reduce any degradation. The use of a barrier on a dental light probe with present attachment devices has been unsatisfactory. It does not allow dental personnel to maintain tension on the barrier and thereby ensure that the light emission is affected as little as possible. As a result, there is a need for a barrier for covering the optical portion of an instrument that can be established in tension and maintained in tension in order to reduce the corruption or degradation of the light beam properties.

Earlier efforts to provide shielding of dental curing lights have also been unsatisfactory from the perspective of contamination caused during removal of the barrier. In many designs, the barriers are designed to fit snugly on the dental curing light or around an appendage of the dental curing light. When the dirty barriers are removed, however, the germs, fluid, blood, etc. on the dirty barriers are often dragged across the dental curing light. This defeats the purpose of the barrier. Consequently, there is a need for a system that will impede germs from contacting the dental curing light during the procedure as well as during removal of the barrier from the dental curing light.

The current invention addresses the problems associated with previous attempts to protect dental curing light equipment from cross-contamination. Perhaps surprising is the fact that the invention can be achieved with such a simple design. That a solution was available, yet unutilized, highlights the long-felt but unsatisfied need for a practical solution in this field. Although those skilled in the art appreciated that a problem existed, perhaps those problems were not fully understood to the extent that the solution was perceived as available. Even though there were a number of approaches taken, those substantial attempts failed to provide an adequate solution. The direction of either a chemical solution or a multiple element cover may have actually taught away from the technical direction of the present invention.

SUMMARY OF THE INVENTION

Accordingly, the present invention provides a solution to the problems encountered in previous attempts to provide cross-contamination protection for dental instruments, especially for dental curing lights. The invention can utilize a unitary, (i.e., single-unit) cover to shield an instrument. Within this cover, an opening can be provided to permit the exchange of heat between the instrument and the surrounding air to provide cooling of the instrument. The opening can be placed on the cover so as to be in the proximity of ventilation components of the device being protected. Furthermore, a perforated opening (i.e., multiple openings in an area of the barrier) can be provided to maximize barrier protection while still allowing sufficient ventilation. The use of a unitary cover avoids the problems that result when two covers are used to protect a dental curing light.

The invention also provides for maintaining a multiple piece instrument in its operational configuration. This is accomplished through a cover that engages at least two pieces of the multiple-pieced equipment and compresses those pieces against one another, thereby establishing them in their operational relationship. In regard to a dental curing light, this aspect of the invention can help retain the light probe in the socket of the dental curing light body.

The invention also provides a system for establishing or maintaining the cover in tension over the dental curing light light probe tip. This smooths the surface of the cover located over the crucial tip portion of the dental curing light light probe. As a result, the smooth surface helps to reduce any degradation of the light beam emitted from the light probe tip. The invention discloses that the cover can be established in tension over the tip portion in a variety of ways. For example, the cover can be pulled against the light probe as a user grips the body portion of the cover. Gripping the cover allows the cover to be pulled tight and smoothed over the light probe tip.

Furthermore, the invention provides a system that permits shielding of an instrument while at the same time permitting circulation of air through the instrument. An intake ventilation opening and exhaust ventilation opening are provided to allow such circulation to occur.

Finally, the invention provides a system for shielding an instrument during removal of the cover. A single unitary cover can be installed, utilized, and then removed. By reversing the cover as the cover is removed, any germs, fluid or blood on the cover is impeded from contaminating the instrument which is being protected during removal of the cover from the instrument (i.e., the likelihood of contamination during the removal process is reduced). Furthermore, by providing ventilation openings in portions of the cover that are not secured to the instrument, the cover can be easily reversed without dragging the dirty cover across the instrument's ventilation openings. This helps reduce the likelihood of contamination of the instrument. Similarly, by utilizing small apertures for the ventilation openings in the cover, the cover does not catch on the instrument being protected, thus avoiding the risk of contacting the instrument with a dirty cover during removal.

Accordingly, it is an object of the invention to provide a system that can provide adequate shielding of an instrument, such as a dental curing light, from contamination while still permitting adequate ventilation of such an instrument. A further object of the invention is to provide shielding that utilizes a single unitary cover but that also provides ventilation of an instrument. Another object of the invention is to provide a system for covering a dental curing light by utilizing a unitary cover for such a device. A further object of the invention is to provide a ventilation opening in a cover in proximity to a ventilation opening in the instrument being protected. Yet another object of the invention is to provide a system of retaining multiple piece instruments in their operational configuration. An object of the invention is to retain a light probe and a curing light body in operational configuration while providing barrier protection at the same time. It is an object of the invention to provide a system for establishing in tension a barrier located on a fiber optic probe tip in tension so as to provide less distortion of the light emitted from the tip. Similarly, it is an object of the invention to establish such tension by merely gripping and slightly pulling against a unitary cover. Furthermore, an object of the invention is to provide a system that permits circulation of air from outside a barrier cover to inside the barrier cover to permit the exchange of heat between the outside air and the instrument being protected. An additional object of the invention is to provide a system for allowing removal of a dirty cover from an instrument being protected while lessening the possibility of contaminating the instrument with the dirty cover during the removal process. A further object of the invention is to do away with any need for an attachment for holding a barrier cover on a light probe portion of a dental curing light. An additional object of the invention is to provide a cost effective barrier protection system for instruments requiring shielding and ventilation. Yet another object of the invention is to provide a system that permits quick and easy installation and removal of a barrier from an instrument, thereby providing more economical turn around time between patients. A specific object of the invention is to provide a unitary cover that will accommodate a variety of dental curing lights which range in size and dimension.

Naturally, further objects of the invention are disclosed throughout other areas of the specification and claims.

DETAILED DESCRIPTION OF THE PREFERRED EMBODIMENTS

Figure 1:
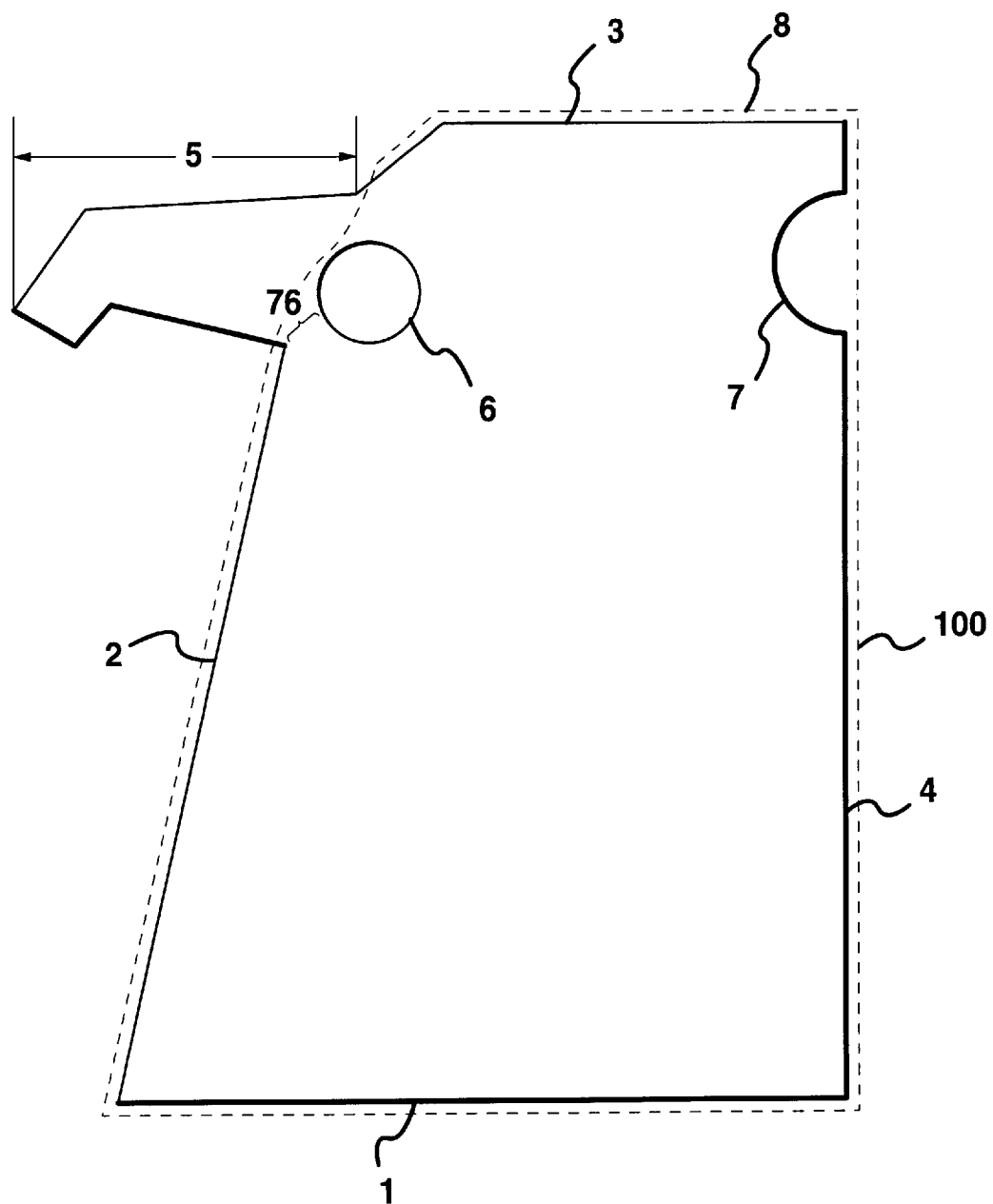
FIG. 1 is a left side view showing the general shape of a unitary infection control barrier system in a flattened position.

With reference now to the drawings, new and improved infection control barrier systems will be described. In one embodiment of the invention, a unitary cover can be utilized to cover an instrument to be protected, such as a dental curing light. This unitary cover can provide shielding protection for the instrument from cross-contamination (i.e., the spread of infection between two different procedures). It should be understood that shielding is intended to mean impeding a patient's germs from contacting the instrument or impeding germs on the device from contacting the patient. A typical unitary cover is shown in FIG. 1 in a form suitable for use with a dental curing light instrument. As noted earlier, a dental curing light can be comprised of a body or handle portion, a light probe portion and a light probe tip portion. A ventilation system is usually provided to cool the dental curing light and usually comprises at least an input port and an exhaust port to allow the circulation of air through the dental curing light. Unitary cover (100) can utilize a plastic material or some other type of alternative material to provide barrier protection. As can be seen in FIG. 1, this unitary cover (100) can have a substantially closed top edge (3) (i.e., an edge that is not necessarily totally closed), a back edge (4) for positioning on the back of a dental curing light instrument, an opening (7) which can be utilized as an exhaust port (i.e., an exhaust ventilation opening) for a dental curing light instrument having a port in such a position. Furthermore, unitary cover (100) can comprise an intake port (6) which can serve as an intake ventilation opening. A front edge (2) can be tapered as seen in FIG. 1. This front edge (2) can taper slightly to allow insertion of a dental curing light into the unitary cover (100). A tip area (5) of the unitary cover (100) can be provided to surround a light probe portion of a dental curing light. Finally, a lower end (1) is open to provide an opening for insertion of a dental curing light into the unitary cover (100). Front edge (2), tip area (5), top edge (3), and back edge (4) all can be sealed to provide a closed cover and greater protection from contamination. In such an arrangement, only lower end (1), intake port (6), and exhaust port (7) would be open to the environment when unitary cover (100) is installed on a dental curing light. It should be understood from this discussion that a unitary cover can be manufactured from more than one piece of material; however, it acts as a single-unit device.

Several factors can be considered in the selection of an adequate material for the cover in order to provide acceptable infection control barrier protection. One of the general criteria for an infection control barrier in dental applications is that the barrier might preferably be made of a water impervious material. Furthermore, the material may be somewhat flexible (to aid in easy installation and removal). Flexibility or the ability to stretch can be affected not only by the choice of material in general but also by the thickness or gauge of that material. Another specific requirement of this application is that the barrier material should be of sufficient clarity around the light probe tip to allow for adequate light transmission (e.g., transparent or translucent material) to ensure proper functioning of the light cure process. The current invention in its present form can utilize clear, low density polyethylene plastic film in a thickness of approximately 1 mil (or 0.001 inch) as a way to accomplish the aforementioned goals or requirements. It is recognized, however, that there are other materials and/or thicknesses and/or combinations that may achieve satisfactory results.

Figure 2:
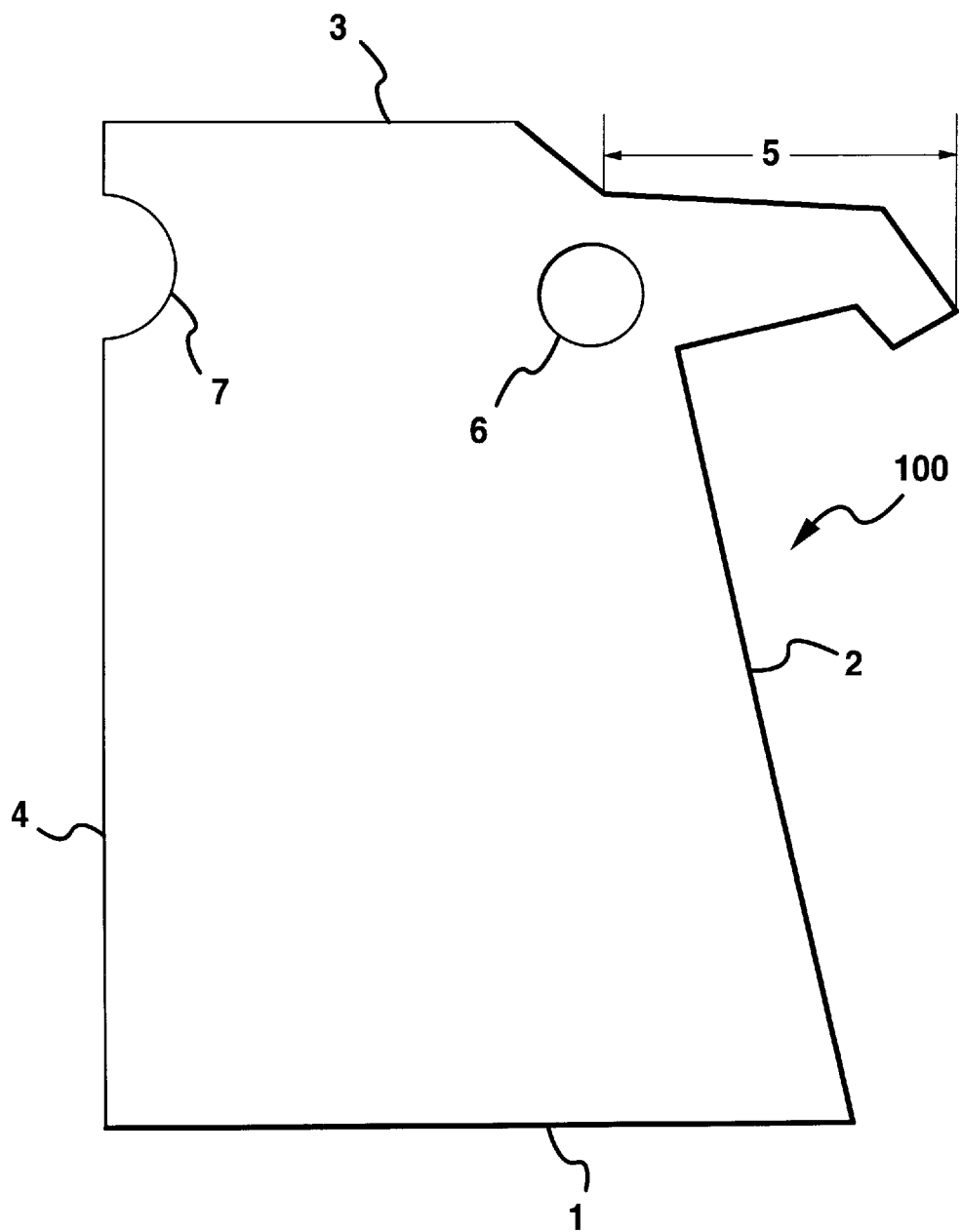
FIG. 2 is a right side view showing the general shape of a unitary infection control barrier system in a flattened position.
Figure 6:
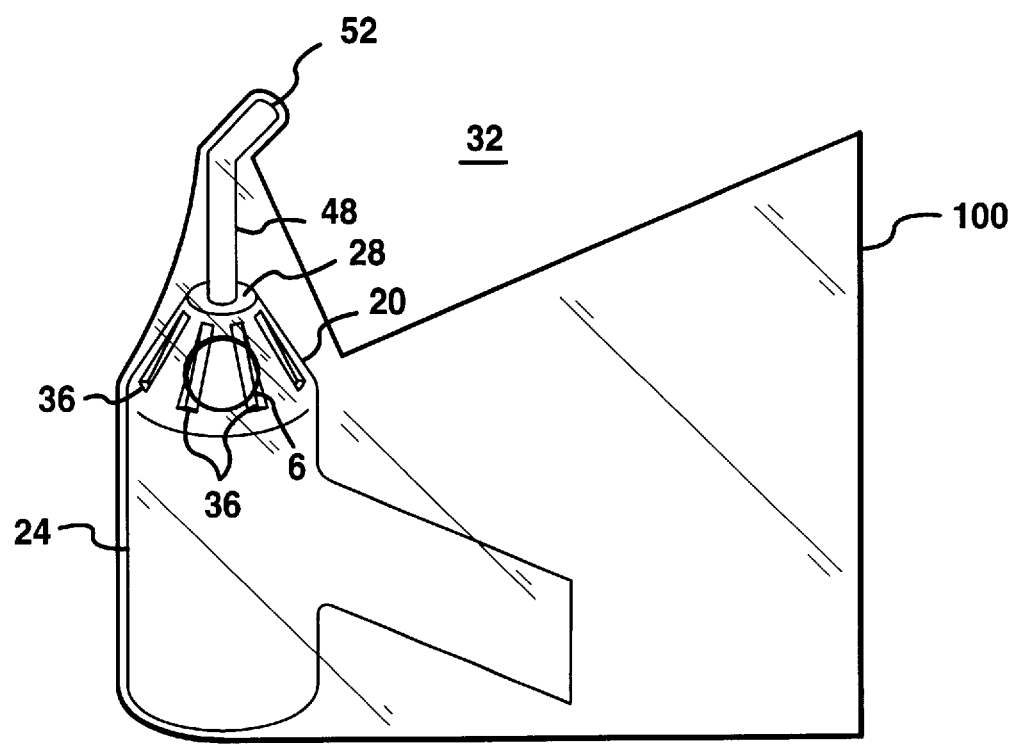
FIG. 6 is a side view of a unitary cover covering a dental curing light instrument.
Figure 8:
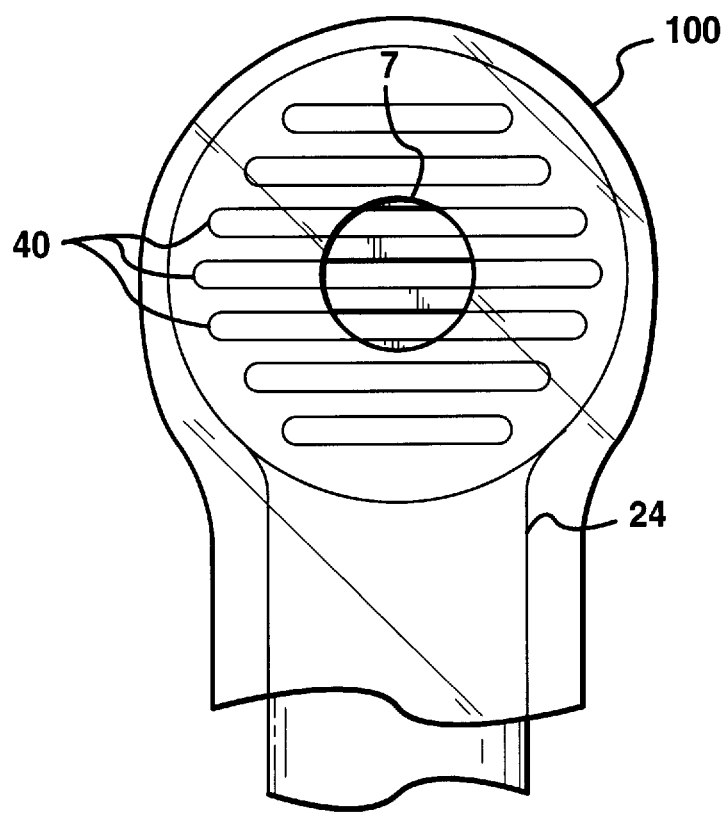
FIG. 8 is a rear view of a unitary cover covering an exhaust opening on a dental curing light instrument showing an exhaust port in the unitary cover.

While FIG. 1 shows a side view of a flattened unitary cover (100), essentially a unitary cover (100) can be created through two pieces of plastic having such a shape. These two pieces can be sealed or melted together on front edge (2), tip area (5), top edge (3), and back edge (4) to provide a sealed arrangement. Furthermore, one can utilize a generally tubular configuration in tip area (5) to accommodate a generally tubular dental curing light probe. (A generally tubular configuration is intended to mean a configuration that resembles a tubular configuration but not limited to a geometrically precise tubular configuration.) Ventilation openings can be provided at intake port (6) on either side of the intake opening (36) of the dental curing light installed within this unitary cover (100), as shown in FIG. 6. Furthermore, an exhaust port (7) in unitary cover (100) can be provided at the back side of a dental curing light installed within the unitary cover (100) as shown in FIG. 8 to cover rear ventilation opening (44) (i.e., a rear exhaust port of the dental curing light). FIG. 2 shows a right side view of unitary cover (100) and shows that its dimensions are similar to the left side view shown in FIG. 1.

Figure 4:
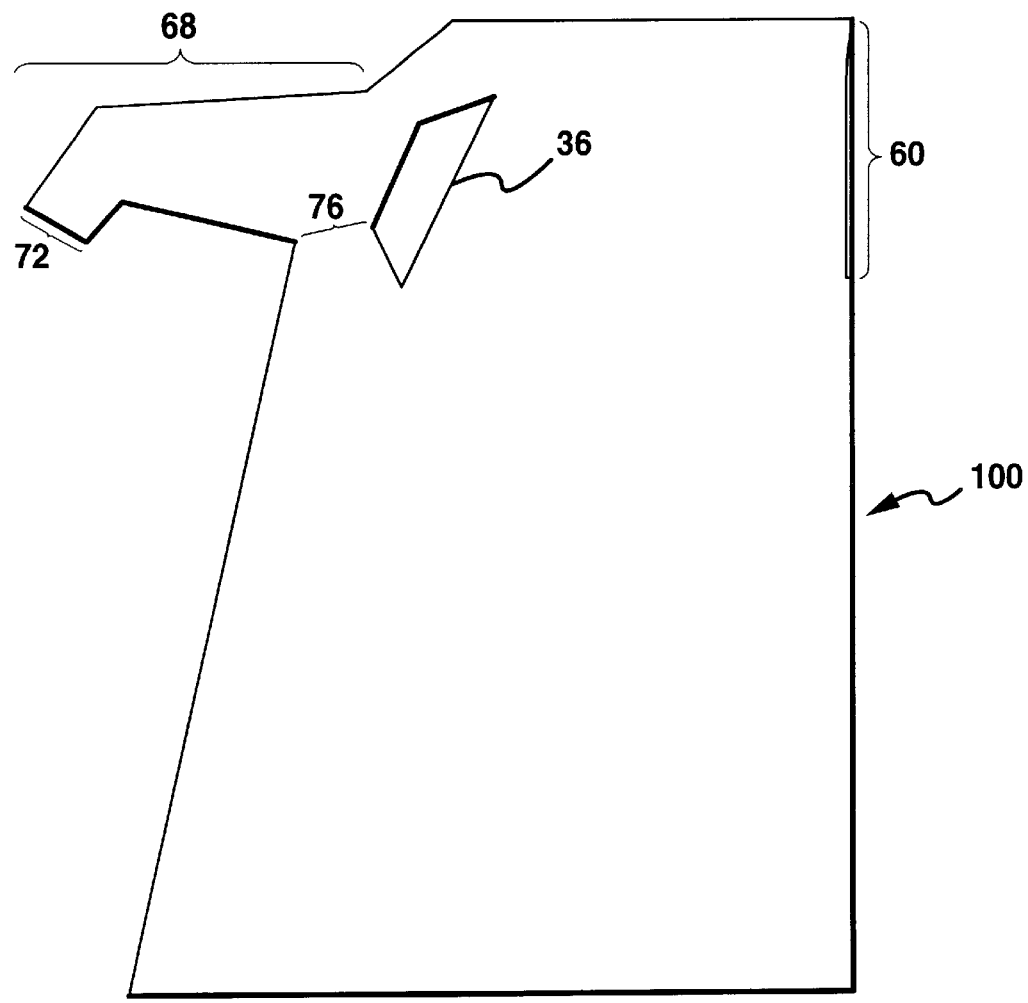
FIG. 4 is a right side view of a unitary infection control barrier system in a flattened position showing alternative ventilation openings including a slit arrangement.

An alternative embodiment of the invention can be seen in FIG. 4. In this embodiment, an intake port (6) can be provided as a ventilation opening in the cover for positioning near a ventilation opening on an instrument. Furthermore, an open slit (60) on the rear of the unitary cover (100) can be used to allow for ventilation at the rear of the unit. A slit would allow exhaust air to push the sides of the slit open to the degree necessary. Therefore, it would efficiently establish the proper size opening needed for ventilation and consequently minimize the amount of surface area left open to the environment. Naturally, a slit could be used for either intake or exhaust in a cover.

As mentioned earlier, dental light cure equipment generally utilizes an internal cooling or ventilation system. Therefore, ventilation can be provided with components that allow for adequate air flow into and through the equipment. The ventilation components (6) and (7) can be optimally sized and shaped to be located strategically to maximize their effectiveness while at the same time not compromising the infection control capabilities of the system as a whole. The intake ventilation component (6) can be situated toward the front of the barrier to allow air to enter into the cooling system of the light cure equipment. The exhaust ventilation component (7) can then be situated at the rear to allow for the exit of the flow of cooling air from the system. In this manner, exhaust ventilation component (7) can serve as a rear ventilation opening. However, the size, shape, location, style, etc. of the ventilation components should not overly interfere with or overly complicate the process of installing the system. It should be easily appreciated by a person of ordinary skill in the art that the size, shape, location, style, etc., of the ventilation components could be readily changed or adjusted to accommodate the many variations in light cure equipment.

As can also be easily understood, dimensions can play a very important role in the overall success of this invention. In general it can be seen that controlling or manipulating some basic dimensions can be used as a means to ensure proper fit and therefore proper operation of this unique barrier system. The following is a discussion of some of the areas of individual dimension specifically affecting various aspects of fit and operation as detailed in FIG. 3.

Dimension (a) is the width of the opening along the lower edge of a barrier system. This can be the opening through which the light cure equipment is inserted into the barrier system. This is a relatively wide opening in the design shown. The criteria for this dimension is that it be just wide enough to facilitate easy installation of the barrier system without detracting from the desired fit.

Dimension (b) is the overall height or length of a barrier system. Proper utilization of this dimension provides a way to adequately cover (and thus protect from cross-contamination) the handle or housing unit of the light cure equipment in the area that is handled or touched by dental personnel during a procedure.

Dimension (c) is the width of a barrier system that covers the light emitting portion of the fiber optic tip. Among the desirable aspects controlled by this dimension are a snug fit to prevent movement of a barrier system in this area, and a close unobstructed contact with the fiber optics to allow sufficient light transmission.

Dimension (d) relates to the size of the ventilation component (6). The feature affected by this dimension is the ability of a barrier system to allow adequate quantities of air to enter the cooling system of the light cure equipment.

Dimension (e) controls the size of the ventilation component (7), providing the proper movement or circulation of cooling air flow through the equipment. Another concern of this dimension is that while it should be large enough to provide necessary air flow it should not be so large as to allow the rear of the curing equipment to protrude or stick through (thereby exposing the curing equipment to cross-contamination).

Dimension (f) concerns the proper fit of a system as a whole, allowing easy installation and yet maintaining a snug fit. Proper use of this dimension can maintain a slight tension on the tip portion of a barrier system, helping to keep it in place and prevent unnecessary movement.

Dimension (g) is the distance from the inside corner or edge of a barrier system to the ventilation component (6). This dimension can be somewhat controlled to serve a two fold purpose. First, it may be large enough to provide adequate plastic material in this area for optimum strength of the system (to prevent tearing of a barrier in this area). Second, it may be of sufficient space to allow for the passage of the fiber optic tip through this area during installation of a barrier system to avoid interference with the ventilation component (6). This can help to keep the fiber optic tip of the equipment from protruding through the ventilation component opening instead of being inserted into the tip area of a barrier.

Dimension (h) controls the positioning of the ventilation component (7) allowing it to be properly centered over the vents or ports of the light cure equipment.

Dimension (I) controls the positioning of the ventilation component (6) allowing it to be precisely positioned in relationship to the vents of the light cure equipment, insuring proper cooling of the light cure equipment.

Dimension (j) is directly related to the size, shape, and length of the light cure equipment's fiber optic tip.

Dimension (k) is affected by the size, shape, and angle of the fiber optic tip.

Figure 7:
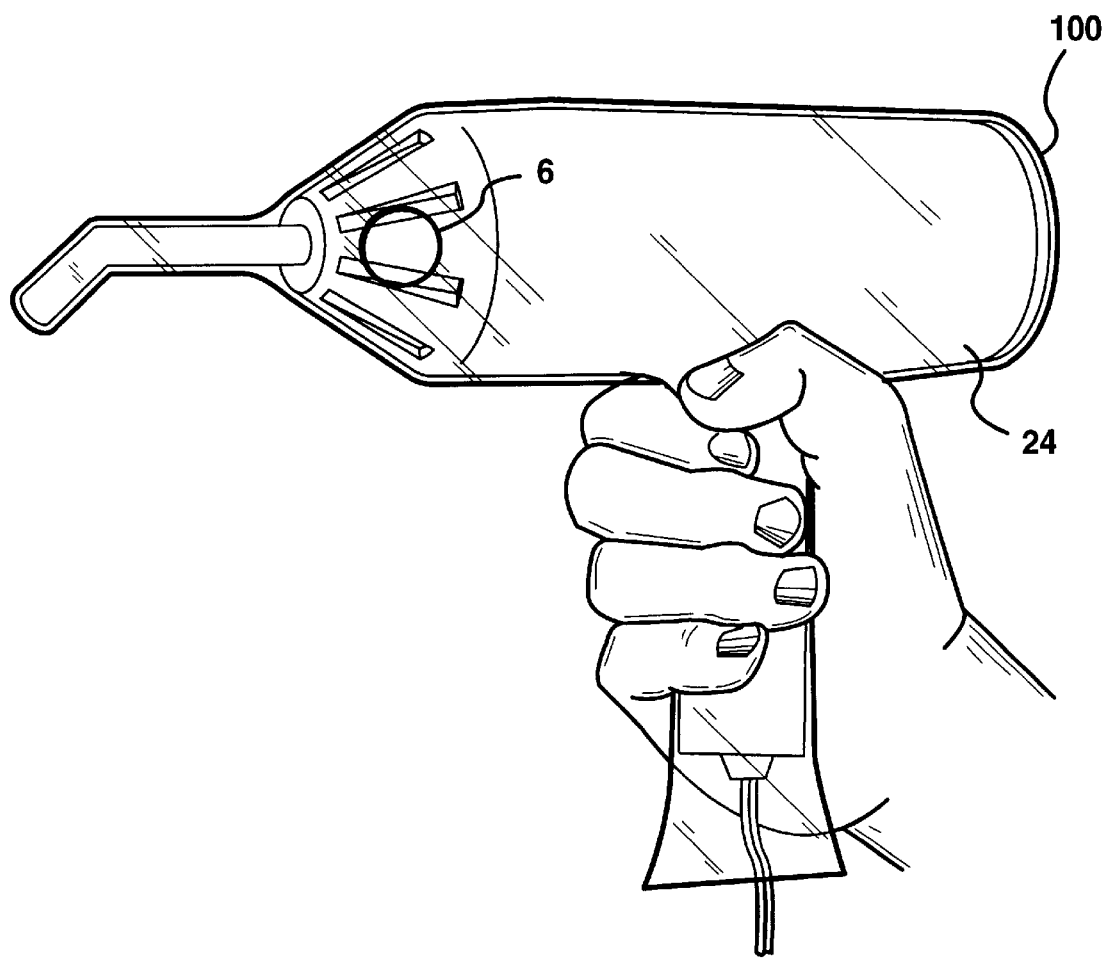
FIG. 7 is a side view of a unitary cover covering a dental curing light instrument in the hand of an operator.

To utilize one embodiment of the invention, one can first insert an instrument, such as a dental curing light, into unitary cover (100). The dental curing light can be inserted through the opening on lower edge (1). Then, the dental curing light can be located within unitary cover (100) as shown in FIG. 6. In this configuration, a unitary cover (100) provides barrier protection for substantially the entire dental curing light (20) by substantially enclosing the dental curing light. (Substantially enclosing is intended to mean surrounding at least a majority of the surface area of an element and is not limited to surrounding the entire element.) Not only is the dental curing light body (24) protected, but also the dental curing light light probe (48) is protected as well. Essentially a dental curing light body portion (8) of the unitary cover substantially covers the body of the dental curing light; a dental curing light light probe cover portion (5) of the unitary cover substantially covers the light probe of the dental curing light; and, a dental curing light light probe tip cover portion (72) of the unitary cover substantially covers the light probe tip of the dental curing light. (Substantial coverage as used here is considered to be greater than fifty percent of the surface area of the element being covered.) As can be seen in FIG. 7, when an operator grips the dental curing light body (24) which is covered by unitary cover (100), the unitary cover can be pulled against the dental curing light light probe (48) and the dental curing light light probe tip (52) to establish the light probe tip cover portion of unitary cover (100) in tension. This tension is created from the force from the operator pulling on the body cover portion of the unitary cover (100) while the dental curing light light probe tip resists the force. As a result, the dental curing light light probe tip portion of the unitary cover can be pulled taut over the dental curing light light probe tip. By pulling taut this portion of the unitary cover, the unitary cover can be smoothed out over the light probe tip. It should be understood that "smooth" is not meant to mean perfectly smooth, but rather generally smooth, so that uneven surfaces that result in inadequate light transmission through the cover for are eliminated. Similarly, "smoothed out" is understood to mean a change in the surface quality of the cover material that leads to an improvement in the light transmission properties of the material being used for protecting the dental curing light light probe tip when those properties are compared to the transmission properties of a loose fitting cover. The smoothing process can be facilitated by utilizing a plastic or other similar material that is stretchable. Stretching can be accomplished either when a cover that is initially smaller than the dental curing light is installed and stretched to conform to the curing light; or stretching can be accomplished by pulling tight against the body cover portion of the unitary cover once the cover is installed.

As can be seen in FIG. 7, one embodiment of the invention allows for intake port (6) of the unitary cover (100) to be positioned in proximity to ventilation openings on the dental curing light (e.g., the intake opening of the dental curing light). As can be seen in FIG. 8, exhaust port (7) on unitary cover (100) can be positioned in proximity to a ventilation opening as well (e.g., exhaust opening (40)) after installation of unitary cover (100) on the dental curing light (20). In this fashion, the unitary cover can permit air to be exhausted from the dental curing light and can allow cooling to occur. With unitary cover (100) in place on dental curing light (20) as shown in FIG. 7, dual goals of the invention are achieved: barrier protection is provided to prevent contamination; and, ventilation is permitted by ventilation openings in the unitary cover.

Another embodiment of the invention shields an instrument, (e.g., a dental curing light) by covering at least a portion of the instrument with a cover in an ambient air environment. A ventilation opening (e.g., an intake port or an output port) is provided in the cover to permit the exchange of heat between the dental curing light and the air. Typically, the dental curing light will be producing an excess amount of heat that needs to be removed to the ambient environment—rather than receiving heat from the environment. Therefore, as the air (32) is circulated either through the dental curing light (20) or flows in proximity to the dental curing light on the inside surface of the cover, heat can be permitted to be exchanged between the air and the dental curing light. (Heat can also be exchanged between the incoming air and any warmer air already inside the covering.)

To accomplish the process of providing ventilation, a ventilation opening (e.g., an exhaust port or an intake port) can be located on a cover and placed in proximity to either a heat producing element, or an element which needs to receive heat. Typically, as can be seen in the case of a dental curing light, such a ventilation opening (e.g., exhaust port (7)) can be placed in proximity to an exhaust opening (40) of a dental curing light (20). It should be understood that proximity in the context of locating a ventilation opening should be understood to mean locating the cover opening close enough to the instrument opening to allow ventilation to occur. In this fashion, air can be vented from the exhaust opening (40) of the dental curing light through exhaust port (7) of the cover to the ambient environment. Similarly, a ventilation opening (e.g., intake port (6)) can be provided in proximity to an intake opening (36) on the curing light (20). In such an arrangement, intake port (6) could provide cooler air to the dental curing light and that air could receive heat from the dental curing light and from air trapped by the cover surrounding the dental curing light.

Figure 5:
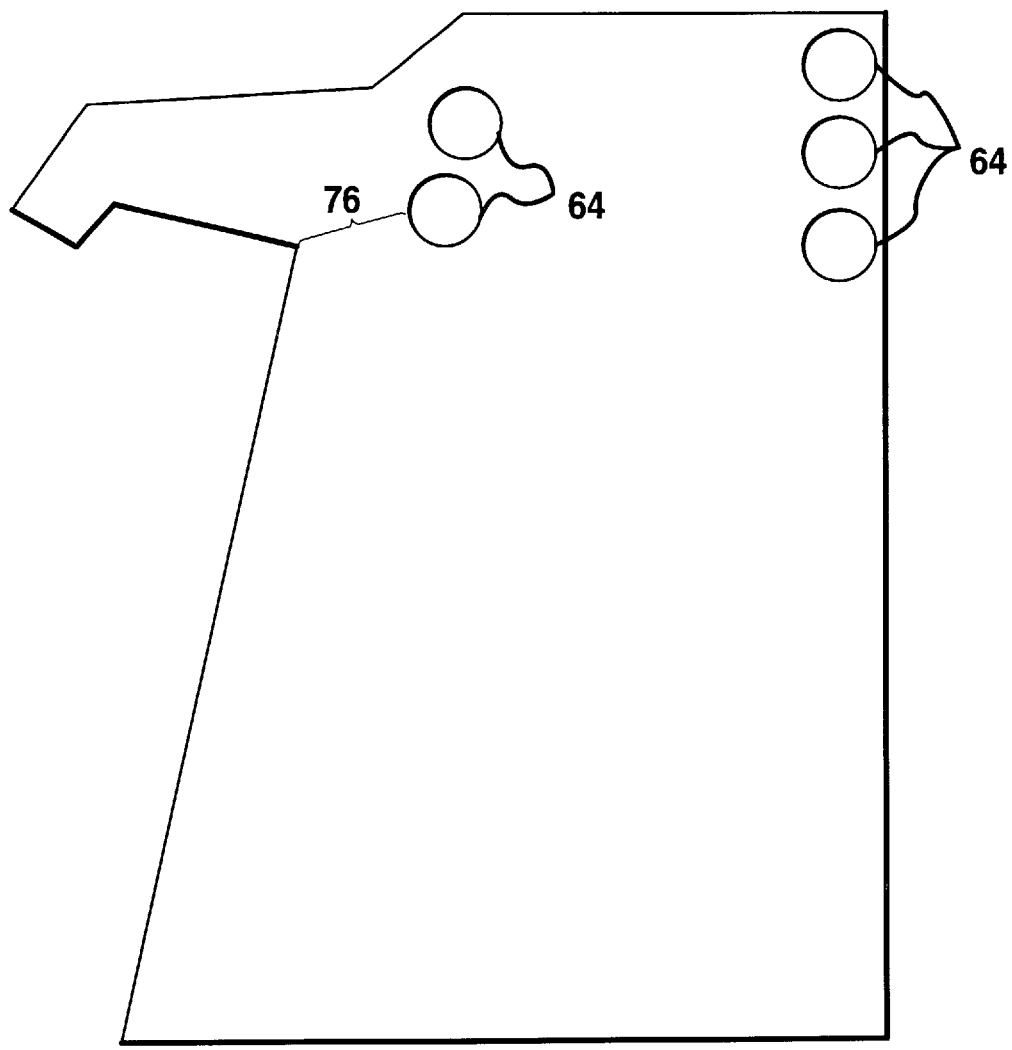
FIG. 5 is a second alternative right side view of a unitary infection control barrier system in its flattened position showing a plurality of ventilation openings.

To accomplish greater barrier protection, it is also feasible to utilize perforations (64) to accomplish a perforated ventilation opening in the cover as shown in FIG. 5. Such a perforated ventilation opening could be comprised of a plurality of small holes. In this manner, an equivalent opening could be provided while at the same time providing a more even distribution of barrier protection over a ventilation opening on the dental curing light. Furthermore, as can be seen in FIG. 8, an exhaust port (7) on unitary cover (100) can be sized small enough to prevent a dental curing light from sliding out through exhaust port (7) and thereby exposing the dental curing light body to greater risk of contamination.

Another embodiment of the invention provides a system that can maintain a multiple piece instrument in proper operational relationship. As can be seen in FIG. 6, unitary cover (100) can place dental curing light body portion (24) in compression with dental curing light light probe portion (48). In this manner, since dental curing light light probe portion (48) is removable from dental curing light body portion (24), unitary cover (100) actually helps maintain the dental curing light light probe portion (48) in its operational relationship with the dental curing light body portion (24). This is accomplished by unitary cover (100) through its engagement with dental curing light light probe (48) as well as the unitary cover's engagement with dental curing light body portion (24). Once the dental curing light light probe is established in its operational position with dental curing light (20), both pieces can be maintained in an operational relationship by unitary cover (100). Due to the tight fit of the unitary cover (100) over the dental curing light, the unitary cover (100) can actually facilitate the operational relationship between the dental curing light light probe and the dental curing light body by compressing the dental curing light light probe with the dental curing light light probe socket (28), as shown in FIG. 9.

Figure 3:
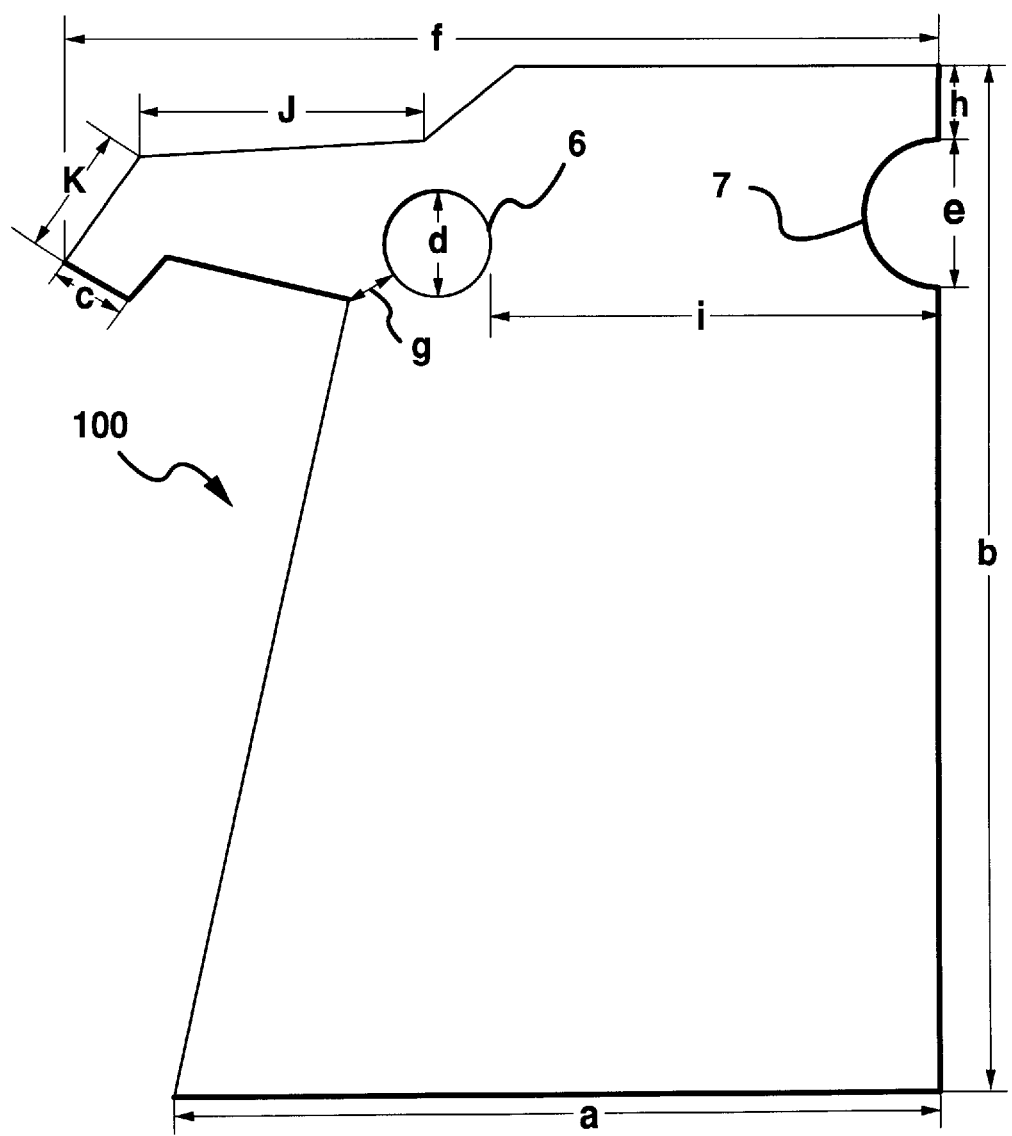
FIG. 3 is a left side view of a unitary infection control barrier system detailing specific dimensions.

One embodiment of the invention can utilize a design that facilitates insertion of a dental; curing light into a unitary cover (100). One aspect of this design is a taper, which is shown in FIG. 1. This taper can begin, as shown in FIG. 3, at the top corner of front edge (2) in proximity to intake port (6). This taper can then extend out to meet lower end (1). The taper can cause the cover to constantly or continuously converge in width from the bottom edge to the top edge. Due to this taper, an L-shaped dental curing light can be inserted into unitary cover (100) as shown in FIGS. 12, 13, 14 and 15.

Figure 9:
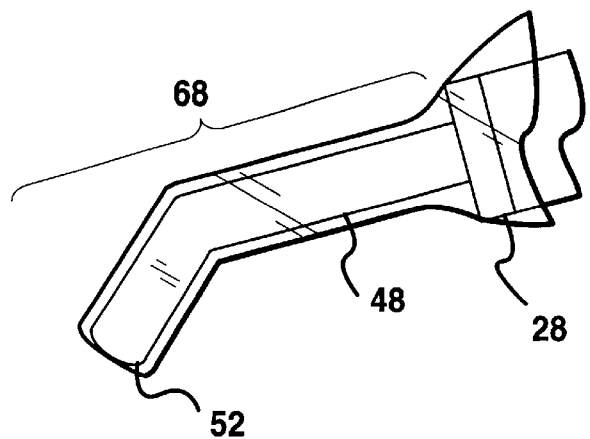
FIG. 9 is a close-up view of the light probe in FIG. 7 showing the unitary cover arrangement over the light probe and light probe tip.
Figure 10:
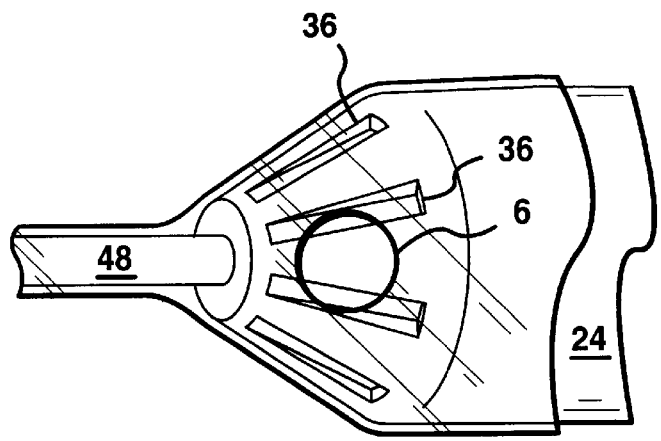
FIG. 10 is a close-up view of an intake opening of the dental curing light instrument in FIG. 7 showing an intake port in the unitary cover.
Figure 11:
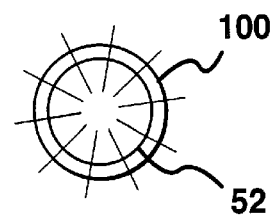
FIG. 11 is a front view taken looking directly into a light probe tip showing light being emitted through a transparent unitary cover.

To accomplish a tight fit between the unitary cover (100) and the dental curing light light probe, a tubular region (68) can be provided in unitary cover (100) as shown in FIG. 9. As can be seen in FIG. 9, this tubular region (68) can conform to the dental curing light light probe (48). This is especially useful for the dental curing light as a tight fit can help to establish a tight fit at dental curing light light probe tip (52), from which light is actually emitted. It is preferred to have as smooth a cover surface as possible at dental curing light light probe tip (52) in order to lessen any corruption of the light emitted from the light probe tip.

As can be seen in FIG. 1 and FIG. 9, tubular region (68) can be angled to conform to a dental curing light light probe (48). This shape can provide a better fit for the instrument. (It could also be useful as a separate cover for a light probe as it could ensure a more snug fit.) As a result, the tubular region is less likely to bunch up or slide off of the light probe tip, which can lead to improved performance. The tubular region (68) can be comprised of a generally tubular region body as well as a distal end (72). Namely, the distal end (72) is part of the tubular region that interfaces with the dental curing light light probe tip (52). The generally tubular region and the distal end substantially cover the generally tubular body region and light probe tip. Again, substantially cover is intended to mean cover at least a majority of the surface area of the element.

While it is easy to appreciate that one needs to prevent contamination of a dental curing light or other instrument during actual use of such an instrument in the mouth of a patient, others appear not to have appreciated the need to protect the same dental curing light from contamination after the procedure when the dirty cover is removed. One embodiment of the invention accomplishes both of these aspects of protection: shielding during use on a patient, as well as shielding during removal of the dirty cover. This can be accomplished by first covering the instrument with a unitary cover (100) having an outside surface as well as an inside surface. The outside surface of the unitary cover is exposed to the environment and the inside surface of the unitary cover is installed in proximity to the dental curing light. The cover impedes the contact of germs with the dental curing light. Then, the dental curing light is used on a patient. After the procedure is completed, the unitary cover can be removed from the dental curing light. To accomplish this, the cover can be substantially reversed during the removal process such that the majority of the inside surface is substantially turned inside-out thus becoming the outside surface of the unitary cover. It should be understood that substantially inside-out is understood to mean that at least a majority of the cover is turned inside-out. In this fashion, the inside surface and the outside surface substantially reverse positions from those positions that were established in the step of covering the instrument. Moreover, germs that were located on the outside surface of the unitary cover after the step of utilizing the instrument can be impeded from contacting the instrument as it is removed from the instrument. (It should be understood that "impede" is understood to mean "lessen the possibility of contact" under these circumstances.) Essentially, these germs are substantially enclosed by the reversed unitary cover, thus avoiding any risk of inadvertent contact between the dirty side of the unitary cover and the clean dental curing fight. In this fashion, as well, any fluid located on the unitary cover is impeded from contacting the instrument as the unitary cover is removed.

The reversal of the cover can be facilitated by a design that releasably attaches to the dental curing light at only one point. In this fashion, there is greater freedom to reverse the cover. Then, the cover can be pulled away from the dental curing light at the attachment as a final step in the removal process. When covering a dental fight probe with a cover, it is preferred to releasably attach the cover at the fight probe. It should be understood that releasably attaching is understood to mean a form of attachment (e.g., by the tension of the cover over the end of the light probe tip or perhaps by some other attachment that resists sliding of the cover on the curing light probe) that establishes attachment that can be released or removed when the operator desires. Prior designs have covered the body of a curing fight by substantially surrounding the body of the curing lights at both ends, for example around one of the appendages. This can inhibit reversal and results in the dirty cover being dragged across the curing light body. A second way to facilitate reversal is to use a cover with a substantially straight back edge (4). Because the back edge is substantially straight (i.e., it does not have any significant corners that can catch on the curing fight body) it is easily removed over the rear end of the dental curing fight and there is less likelihood that it will catch on any of the dental curing light's appendages. Similarly, a non-expanding, continuously converging, or constantly converging back edge could accomplish the same result and facilitate reversal. A non-expanding back edge would be viewed as a cover that is devoid of corners that can catch on the appendage (e.g., the rear appendage) of a dental curing light. It should be appreciated that the dimensions disclosed in the drawings can be manipulated to facilitate reversal as well. It should be readily apparent to a person of ordinary skill in the art that some of these dimensions can cooperate to facilitate the reversal process. Again, this is a great improvement over prior designs which actually fastened the cover to the rear end or appendage of the dental curing fight body and hindered reversal rather than facilitated reversal. By sizing the ventilation opening to be smaller than the appendage, the cover will not slide over the appendage. Similarly, reversal is facilitated by not retaining the unitary cover at a ventilation opening of the dental curing light, as it is therefore less likely that the dirty cover will be in close proximity to the instrument when the cover is removed.

Figure 16:
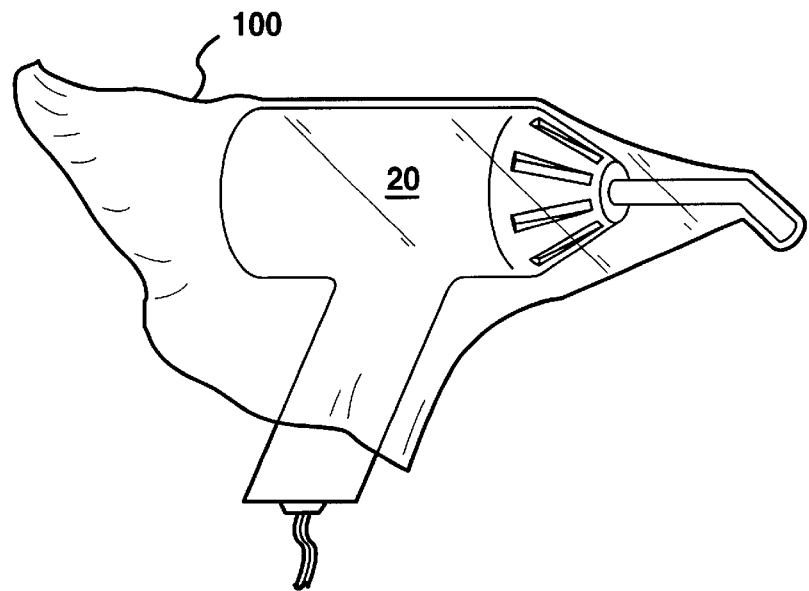
FIG. 16 is a first step in removing a unitary cover from the operational position on the dental curing light instrument showing the cover being reversed as it is removed from the instrument.
Figure 17:
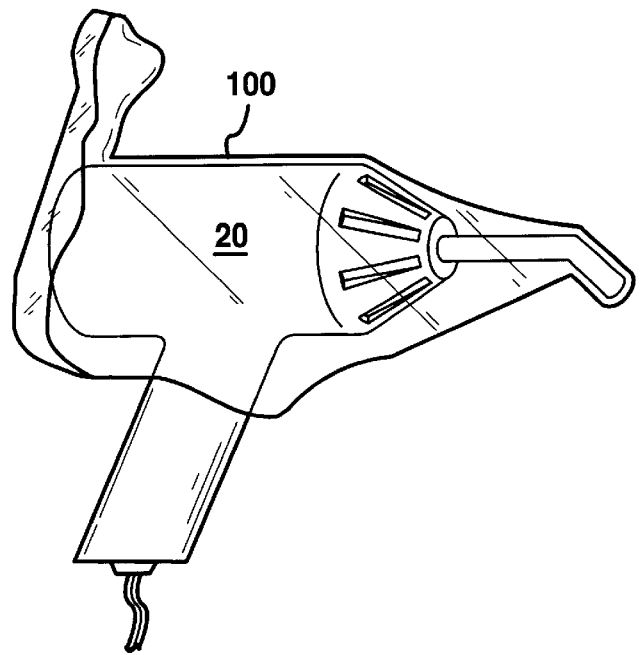
FIG. 17 is a subsequent view to FIG. 16 showing the unitary cover being removed from the dental curing light instrument and continuing to be reversed as it is removed from the dental curing light instrument.
Figure 18:
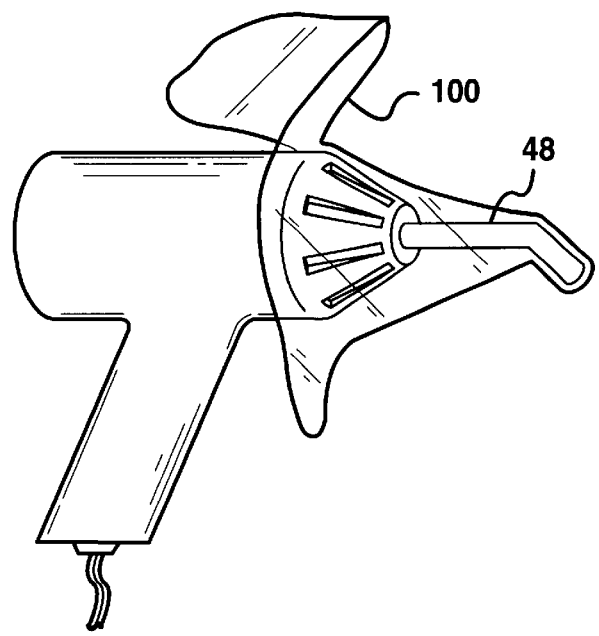
FIG. 18 is a view of the removal process of the unitary cover from the dental curing light instrument subsequent to that shown in FIG. 17.
Figure 19:
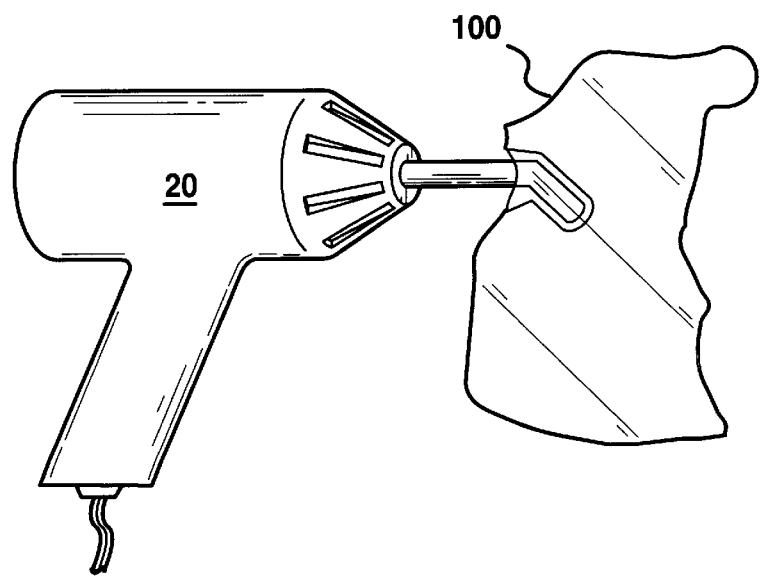
FIG. 19 is a view showing a final step in the process of removing the unitary cover from the dental curing light instrument, showing a substantially reversed unitary cover still partially covering the light probe tip of the dental curing light instrument.

The reversal process is shown in FIGS. 16, 17, 18 and 19. While the following is the preferred method of reversing the cover, there are obviously a variety of reversal steps that could be followed. Therefore, this description of the reversal process is not intended to be limiting to the preferred embodiment; but rather, should encompass all similar reversal methods. In FIG. 16, the unitary cover is gripped at its bottom edge and pulled up along the dental curing light body portion (24), thus initiating reversal of the unitary cover (100). As can be seen in FIG. 16, the upper open end is turned inside out. Next, as shown in FIG. 17, the unitary cover is turned further inside out and pulled toward the dental curing light light probe. In FIG. 18, the unitary cover is substantially turned inside out. Finally, in FIG. 19, the unitary cover, except for the portion covering the end of the dental curing light light probe, has been turned nearly completely inside out, such that what was previously the inside surface of the unitary cover has become the outside surface.

Figure 12:
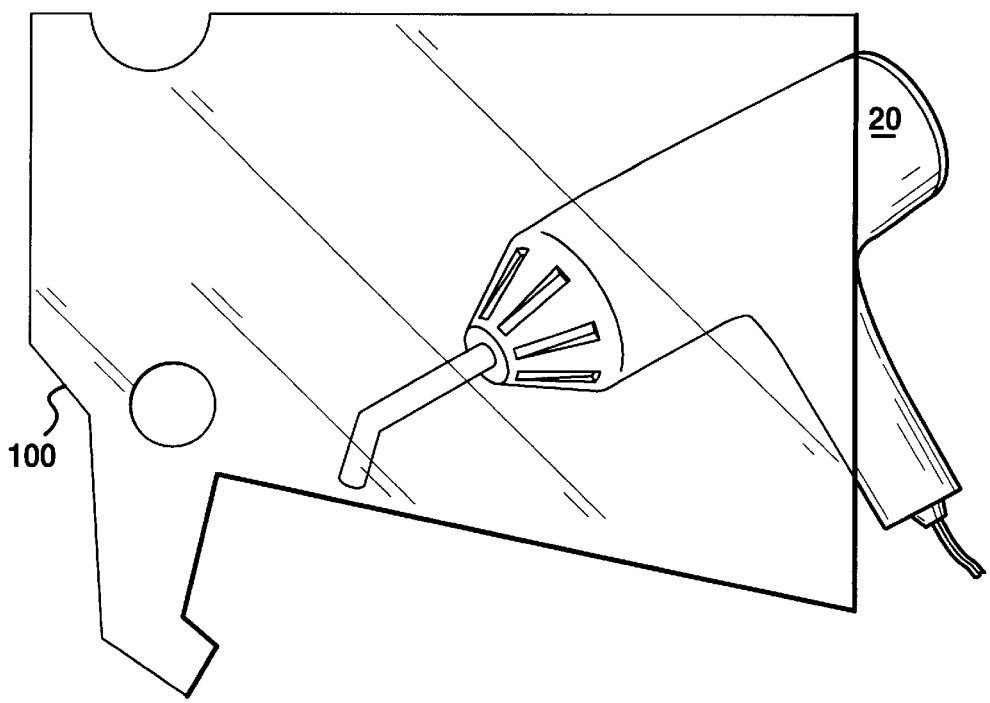
FIG. 12 is a view showing a first step of insertion of a light curing instrument into a unitary cover.
Figure 13:
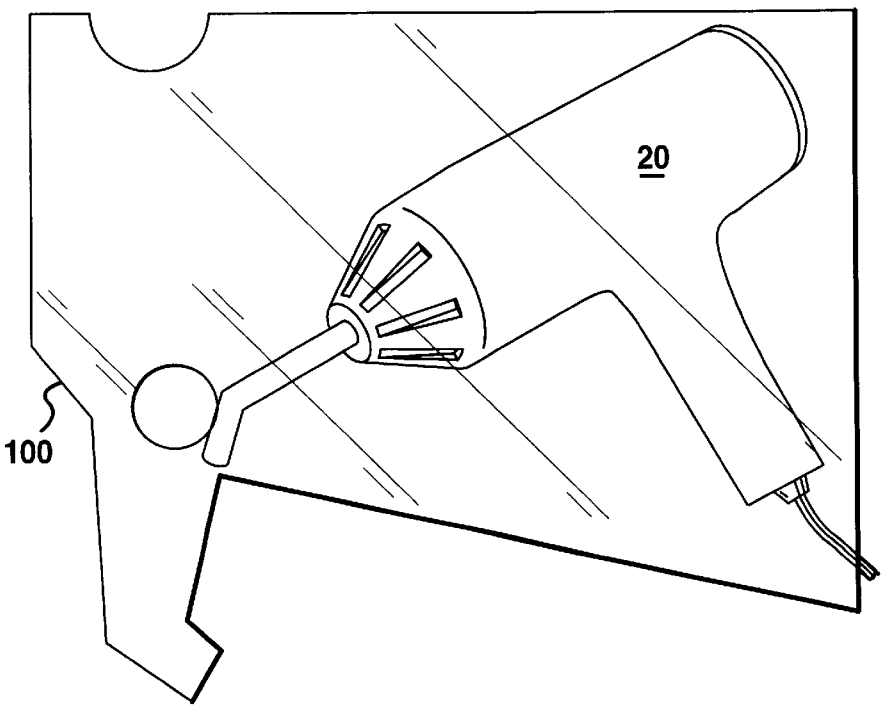
FIG. 13 is a view showing insertion of a light curing instrument into a unitary cover at a position where the light tip probe passes a ventilation port in the unitary cover.
Figure 14:
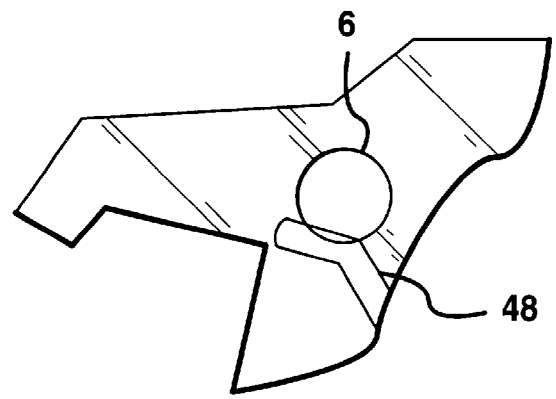
FIG. 14 is a close up view showing a light probe tip passing by a ventilation port in a unitary cover without catching on the opening.
Figure 15:
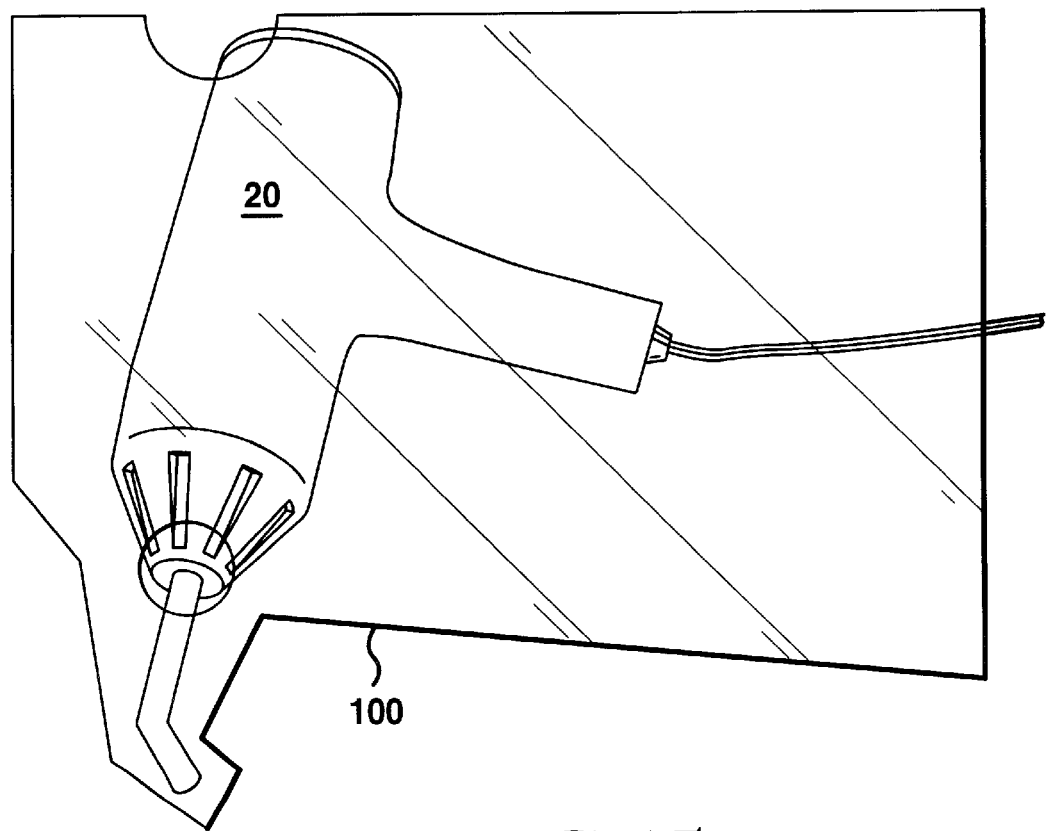
FIG. 15 is a further view showing insertion of the dental curing light instrument into the unitary cover.

An embodiment of the invention showing a method of installing the unitary cover (100) can be seen FIGS. 12, 13, 14, and 15. In FIG. 12, a dental curing light is installed through the open lower end (1) of unitary cover (100). This open lower end (1) allows insertion of dental curing light (20) into the unitary cover. The "L" shaped dental curing light (20) can be installed at an angle to the back edge of the unitary cover to permit the "L" shaped dental curing light to be inserted into the unitary cover. As shown in FIG. 13, the dental curing light (20) is inserted far enough for the dental curing light light probe (48) to be in proximity to intake port (6). As shown in a close-up view of this region in FIG. 14, dental curing light light probe (48) is capable of sliding by intake port (6) without becoming entangled in this opening. This can be accomplished by provision of an uninterrupted region (76) on unitary cover (100) between the upper corner of front edge (2) and the end of tubular region (68) extending towards intake port (6). This uninterrupted region (76) can provide a generally smooth surface for dental curing light probe (48) to slide past. It should be understood that uninterrupted is intended to mean a generally smooth area that does not comprise any holes or rough areas on which a light probe could easily be obstructed. Finally, as shown in FIG. 15, dental curing light (20) can be inserted in a near final position. An actual final position is shown by FIG. 6 which shows dental curing light (20) positioned such that unitary cover (100) substantially covers and substantially encloses the entire dental curing light (20).

The preferred method of manufacturing unitary cover (100) incorporates a die or tool that can use a heater to cut out the general shape of the unitary cover while sealing or melting together the appropriate edges in a single operation. The seal should be relatively strong (so as not to tear easily), and also it should not leak (i.e., it should at least be water impervious). The die also provides a way of cutting out the openings that constitute the ventilation components during the same operation. The finished product can then be an envelope or an enclosure of the proper size and shape which is open on the lower edge (1) and at the ventilation components (6) and (7), but that is sealed along or around the remaining edges. The result is an efficient, cost effective one step process. Use of such a tool or die allows repeatability whereby individual pieces can be manufactured to the same size, shape, and quality, etc. Furthermore, changes in the tool or die can be utilized to adjust the size and shape of the barrier and the placement of the ventilation components to allow for specific fit of different styles, shapes, brands, etc., of dental equipment. It is also feasible that one may manufacture the invention through the use of a mold, as one of ordinary skill in the art would understand.

The foregoing discussion and the claims that follow describe the preferred embodiments of the present invention. Particularly with respect to the claims it should be understood that changes may be made without departing from the essence of the invention. In this regard, it is intended that such changes would still fall within the scope of the present invention. It is simply not practical to describe and claim all possible revisions which may be accomplished. To the extent such revisions utilize the essence of the present invention, each naturally falls within the breadth of protection encompassed by this patent. This is particularly true for the present invention since its basic concepts and understandings are fundamental in nature and can be applied broadly in a variety of ways. Further, it should be understood that various permutations and combinations of the elements shown in the claims are possible and should fall within the scope of this disclosure. Similarly, it should be understood that the invention is closely related to the instrument which it is intended to protect and can embody not only the cover itself, but also, the cover in combination with the instrument.

What is claimed is:

1. A device for shielding a dental curing light, said dental curing light having at least a body portion, a light probe portion, and a light probe tip portion wherein light may be emitted from the light probe tip portion, said device comprising:

(a) a unitary cover for shielding the dental curing light;
   (b) a dental curing light body cover portion of said unitary cover configured for engaging the body portion of said dental curing light;
   (c) a dental-curing-light light-probe cover portion of said unitary cover configured for engaging the light probe portion of said dental curing light; and
   (d) at least one ventilation opening of the unitary cover when installed on the dental curing light; and
   (e) a dental curing light light probe tip cover portion of said unitary cover configured for engaging the light probe tip portion of said dental curing light; wherein said dental curing light light probe tip cover portion of said unitary cover is maintained in tension when said unitary cover is installed on said dental curing light so that said light probe tip cover portion is smoothed out by said tension.

2. A device for shielding a dental curing light as described in claim 1 wherein said dental-curing-light light-probe cover portion of said unitary cover pulls against said dental curing light light probe tip cover portion to establish said dental curing light light probe tip cover portion in tension.

3. A device for shielding a dental curing light as described in claim 2 wherein said dental curing light body cover portion of said unitary cover pulls against said dental-curing-light light-probe cover portion to establish said dental curing light light probe tip cover portion in tension.

4. A device for shielding a dental curing light as described in claim 1 wherein said unitary cover comprises stretchable material and wherein said dental curing light light probe tip cover portion stretches when said unitary cover is installed on said dental curing light.

5. A device for shielding a dental curing light as described in claim 4 wherein said unitary cover is sized smaller than said dental curing light to establish said light probe tip cover portion in tension during installation.

6. A method for shielding a dental curing light, said dental curing light having at least a body portion, a light probe portion, and a light probe tip portion wherein light may be emitted from the light probe tip portion, said method comprising the following steps:

(a) covering said dental curing light with a unitary cover;
   (b) engaging the body portion of said dental curing light with a dental curing light body cover portion of said unitary cover;
   (c) engaging the light probe portion of said dental curing light with a dental-curing-light light-probe cover portion of said unitary cover;
   (d) engaging the light probe tip portion of said dental curing light with a dental curing light light probe tip cover portion of said unitary cover;

(e) maintaining said dental curing light light probe tip cover portion in tension to smooth out said light probe tip cover portion.

7. The method of claim 6 wherein said step of establishing said dental curing light light probe tip cover portion in tension comprises the step of pulling on said dental curing light light probe cover portion of said unitary cover.

8. The method of claim 7 wherein said step of establishing said dental curing light light probe tip cover portion in tension comprises the step of pulling on said dental curing light body cover portion.

9. The method of claim 6 and further comprising the step of stretching said unitary cover during installation of said unitary cover.

10. The method of claim 9 and further comprising the step of utilizing a unitary cover that is initially smaller than said dental curing light.

11. A device for shielding a dental curing light unit usable in an air environment said dental curing light having at least a body portion and a light probe portion, said device comprising:

(a) a unitary cover for substantially enclosing the dental curing light unit;

(b) a dental curing light body cover portion of said unitary cover configured to substantially cover the body portion of the dental curing light when said unitary cover is installed on the dental curing light;

(c) a dental-curing-light light-probe cover portion of said unitary cover configured to substantially cover the light probe portion of the dental curing light when said unitary cover is installed on the dental curing light;

(d) a substantially open bottom of the unitary cover; and (e) at least one opening in said unitary cover separate from the substantially open bottom, said at least one opening configured to permit an exchange of heat between the dental curing light and the air when said unitary cover is installed on the dental curing light.

12. The device for shielding a dental curing light unit as described in claim 11 wherein the dental curing light comprises a heat producing element and wherein said at least one opening in said dental curing light is located on said unitary cover so as to be in proximity to the heat producing element when said unitary cover is installed on the dental curing light.

13. The device for shielding a dental curing light unit as described in claim 11 wherein the dental curing light comprises a ventilation opening and wherein said at least one opening in said dental curing light is located on said unitary cover so as to be in proximity to the ventilation opening when said unitary cover is installed on the dental curing light.

14. The device for shielding a dental curing light unit as described in claim 13 wherein said unitary cover comprises at least one rear ventilation opening.

15. The device for shielding a dental curing light unit as described in claim 13 wherein said unitary cover comprises at least one intake ventilation opening.

16. The device for shielding a dental curing light unit as described in claim 13 wherein said unitary cover comprises at least one exhaust opening.

17. The device for shielding a dental curing light unit as described in claim 13 wherein the dental curing light is substantially "L" shaped and wherein said cover comprises a taper for permitting installation of said cover over the "L" shaped curing light.

18. The device for shielding a dental curing light unit as described in claim 13 wherein said unitary cover comprises a generally tubular region for covering the light probe portion of the dental curing light.

19. The device for shielding a dental curing light unit as described in claim 18 wherein said cover comprises an uninterrupted area between said at least one opening and said generally tubular region to permit installation of the light probe portion into said generally tubular region without catching said dental curing light on said at least one opening.

20. The device for shielding a dental curing light unit as described in claim 19 wherein said uninterrupted region is at least 0.5 cm wide.

21. The device for shielding a dental curing light unit as described in claim 18 wherein said generally tubular region comprises a generally tubular region body and a distal end and wherein said distal end of said generally tubular region is angled from said generally tubular region body to conform to the light probe portion.

22. The device for shielding a dental curing light unit as described in claim 13 wherein said cover is configured to place a portion of said unitary cover in tension over said light probe portion of said dental curing light when said unitary cover is installed on the dental curing light.

23. The device for shielding a dental curing light unit as described in claim 22 wherein said light probe comprises a fiber optic tip and wherein said cover comprises a distal end portion for cover the fiber optic tip of the light probe of said dental curing light and wherein said cover is configured to place said distal end portion in tension when said unitary cover is installed on the dental curing light for creating a substantially smooth surface over said fiber optic tip.

24. The device for shielding a dental curing light unit as described in claim 13 wherein said cover is configured to accommodate a plurality of curing light units having unique dimensions.

25. The device for shielding a dental curing light unit as described in claim 13 wherein said unitary cover is preforated.

26. The device for shielding a dental curing light unit as described in claim 11 wherein said dental-curing-light light-probe cover portion comprises a generally tubular region body and a distal end and wherein said distal end of said generally tubular region is angled from said generally tubular region body to conform to the light probe portion.

27. A method of shielding a dental curing light, said dental curing light having at least a body portion and a light probe portion, said method comprising the following steps:

a) substantially enclosing said dental curing light in a unitary cover, wherein air is located on the opposite side of said cover from said dental curing light;

b) substantially covering body portion of the dental curing light with a curing light body cover portion of said unitary cover;

c) substantially covering the light probe portion of the dental curing light with a dental-curing-light light-probe cover portion of said unitary cover; and d) providing at least one opening in said cover;

permitting the exchange of heat between the dental curing light and the air through said opening.

28. The method of shielding a dental curing light as described in claim 27 wherein the dental curing light comprises a heat producing element and further comprising the step of locating said at least one opening in proximity to said heat producing element.

29. The method of shielding a dental curing light as described in claim 27 wherein the dental curing light comprises a ventilation opening and further comprising the step of locating said at least one opening in proximity to said opening.

30. The method of shielding a dental curing light as described in claim 29 wherein said step of providing at least one opening in said cover for permitting the exchange of heat between the dental curing light and the air further comprises the step of providing at least one rear ventilation opening in said unitary cover.

31. The method of shielding a dental curing light as described in claim 29 and wherein said step of providing at least one opening in said cover for permitting the exchange of heat between the dental curing light and the air further comprises the step of providing at least one intake ventilation opening in said unitary cover.

32. The method of shielding a dental curing light as described in claim 29 and wherein said step of providing at least one opening in said cover for permitting the exchange of heat between the dental curing light and the air further comprises the step of providing at least one exhaust opening in said unitary cover.

33. The method of shielding a dental curing light as described in claim 29 and further comprising the step of accommodating a plurality of uniquely sized curing lights.

34. The method of shielding a dental curing light as described in claim 29 and further comprising the step of providing pluralility of openings in said unitary cover.

35. A device for shielding a dental curing light probe, said dental curing light light probe having a generally tubular body region and a fiber optic probe portion wherein said fiber optic probe portion is angled from said generally tubular body portion, said device comprising:

(a) a generally tubular light probe body cover portion configured to substantially cover the generally tubular body region of a dental curing light; and (b) a dental curing light light probe cover portion configured to substantially cover the light probe of the dental curing light, wherein said light probe cover portion is angled from said light probe body cover portion.

36. A device for shielding a dental curing light, said dental curing light having at least a dental curing light body portion and a dental curing light light probe portion, said device comprising:

(a) a unitary cover for covering said dental curing light;

(b) a dental curing light body cover portion of said unitary cover for covering said body portion of the dental curing light;

(c) an inside surface of said unitary cover, said inside surface located in proximity to the dental curing light when said unitary cover is installed on the dental curing light;

(d) at least one ventilation opening of the unitary cover when installed on the dental curing light; and (e) an outside surface of said unitary cover, said outside surface exposed to the environment when said unitary cover is installed on the dental curing light; wherein said unitary cover is configured to facilitate reversing during removal from the dental curing light to impede any germs located on said outside cover from contacting the dental curing light.

37. The device for shielding a dental curing light as described in claim 36 and further comprising a dental-curing-light light-probe cover portion of said unitary cover for covering said light probe portion of the dental curing light.

38. A device for shielding a dental curing light as described in claim 36, wherein said unitary cover is releasably attached at only one position on the dental curing light when said cover is installed on the dental curing light.

39. A device for shielding a dental curing light as described in claim 36, wherein said unitary cover comprises a substantially straight back edge for facilitating removal of said unitary cover from the dental curing light.

40. A device for shielding a dental curing light as described in claim 36, wherein said at least one ventilation opening does not retain said unitary cover on said dental curing light when said unitary cover is installed on said dental curing light.

41. A device for shielding a dental curing light as described in claim 36, wherein said at least one ventilation opening is positioned in proximity to an appendage of the dental curing light body when said unitary cover is installed on said dental curing light and wherein said at least one ventilation opening is smaller than said appendage.

42. A device for shielding a dental curing light as described in claim 36, 37, 40, or 41 wherein said dental curing light comprises an intake opening and wherein said at least one ventilation opening of said cover is configured for installation in proximity to said intake opening.

43. A device for shielding a dental curing light as described in claim 36, 37, 40, or 41, wherein said dental curing light comprises an exhaust opening and wherein said at least one ventilation opening of said unitary cover is configured for installation in proximity to said exhaust opening.

44. A device for shielding a dental curing light as described in claim 36, 37, 40, or 41, wherein said dental curing light comprises a heat producing element and wherein said at least one ventilation opening of said unitary cover is configured for installation in proximity to said heat producing element.

45. A device for shielding a dental curing light as described in claim 36, 37, 40 or 41 wherein said dental curing-light light-probe cover portion is configured to establish firm engagement with said dental curing light light probe portion when said unitary cover is installed on said dental curing light.

46. A method of shielding a dental curing light, said dental curing light having at least a dental curing light body portion and a dental curing light light probe portion, said method comprising the steps of:

(a) covering the curing light with a unitary cover having an outside surface and an inside surface, wherein said outside surface is exposed to the environment and said inside surface is located in proximity to the dental curing light;

(b) covering the dental curing light body portion with a dental curing light body cover portion of said unitary cover;

(c) covering the dental curing light light probe portion with a dental-curing-light light-probe cover portion of said unitary cover;

(d) providing at least one ventilation opening in said unitary cover;

(e) releasably attaching said unitary cover to said dental curing light;

(f) utilizing said dental curing light; and then (g) removing said unitary cover from said dental curing light by facilitating substantial reversal of said unitary cover so that said unitary cover is turned substantially inside-out;

whereby germs located on said outside surface of said unitary cover after said step of utilizing are impeded from contacting the dental curing light.

47. The method of shielding a dental curing light as described in claim 46 wherein said step of providing at least one ventilation opening comprises the step of not utilizing said ventilation opening for retaining said unitary cover on said dental curing light.

48. The method of shielding a dental curing light as described in claims 46 or 47 wherein said step of securing said unitary cover to the dental curing light comprises the step of securing said unitary cover to said dental curing light light probe portion.

49. The method of shielding a dental curing light as described in claim 48 wherein said step of removing comprises the steps of:

(g1) gripping said unitary cover at a bottom edge; and then (g2) pulling said unitary cover over said dental curing light body portion toward said dental curing light light probe portion.

50. A method of shielding a dental curing light having at least a dental curing light body portion and a dental curing light light probe portion, said method comprising the steps of:

(a) inserting said dental curing light within a unitary dental curing light cover;

(b) inserting the light probe portion of said dental curing light in a light probe portion of said unitary dental curing light cover;

(c) inserting the body portion of said dental curing light in a dental curing light body portion of said unitary dental curing light cover;

(d) pulling on said dental curing light body portion of said unitary dental curing light cover so as to establish a tight fit between the dental curing light probe portion and said light probe portion of said unitary dental curing light cover.

51. A device for shielding a dental curing light said dental curing light having at least a body portion, a light portion probe, and a light probe tip portion, said device comprising:

(a) unitary cover;

(b) an open bottom edge of said unitary cover;

(c) a substantially closed top edge of said unitary cover;

(d) a body cover portion of said unitary cover for substantially covering the dental curing light body portion;

(e) an exhaust portion in said unitary cover configured for allowing the exhaust of air through said unitary cover; and (f) a light probe cover portion of the unitary cover.

52. A device for shielding a dental curing light as described in claim 51 and further comprising:

a generally tubular light probe cover portion of said unitary cover for covering the dental curing light light probe portion, and a light probe tip cover portion for covering the dental curing light light probe tip portion.

53. A device for shielding a dental curing light as described in claim 52 and further comprising a angle tip of said light probe cover portion.

54. A device for shielding a dental curing light as described in claim 51 or 52 wherein said body cover portion of said unitary cover comprises a continuously converging portion converging in width from said bottom edge of said unitary cover to said top edge of said unitary cover.

55. A device for shielding a dental curing light as described in claim 54 and further comprising an intake port in said unitary cover configured for allowing the intake of air through said unitary cover.

56. A device for shielding a dental curing light as described in claim 51 and further comprising an intake port in said unitary cover configured for allowing the intake of air through said unitary cover.

* * * * *